United States Patent
Duplessis et al.

(10) Patent No.: US 8,257,441 B2
(45) Date of Patent: Sep. 4, 2012

(54) INTERVERTEBRAL DISC PROSTHESIS

(75) Inventors: Stephan J. Duplessis, Calgary (CA); Lall Sekhon, Reno, NV (US); John R. Hurlbert, Calgary (CA)

(73) Assignee: Kinetic Spine Technologies, Inc., Calgary, Alberta (CA)

( * ) Notice: Subject to any disclaimer, the term of this patent is extended or adjusted under 35 U.S.C. 154(b) by 1261 days.

(21) Appl. No.: 11/978,804

(22) Filed: Oct. 30, 2007

(65) Prior Publication Data

US 2008/0058944 A1 Mar. 6, 2008

Related U.S. Application Data

(63) Continuation of application No. PCT/CA2006/000676, filed on May 2, 2006.

(60) Provisional application No. 60/594,730, filed on May 2, 2005.

(51) Int. Cl.
*A61F 2/44* (2006.01)
(52) U.S. Cl. ........... 623/17.15; 623/17.16; 623/20.26
(58) Field of Classification Search .... 623/17.11–17.16, 623/20.26
See application file for complete search history.

(56) References Cited

U.S. PATENT DOCUMENTS

| | | | | |
|---|---|---|---|---|
| 3,934,272 | A | * | 1/1976 | Wearne et al. ............. 623/20.26 |
| 4,064,568 | A | * | 12/1977 | Grundei et al. ............ 623/20.26 |
| 4,216,549 | A | * | 8/1980 | Hillberry et al. .......... 623/20.26 |
| 5,562,738 | A | * | 10/1996 | Boyd et al. ................. 623/17.15 |
| 6,179,874 | B1 | * | 1/2001 | Cauthen .................... 623/17.14 |
| 6,402,785 | B1 | * | 6/2002 | Zdeblick et al. ........... 623/17.16 |
| 6,440,168 | B1 | * | 8/2002 | Cauthen .................... 623/17.14 |
| 6,572,653 | B1 | | 6/2003 | Simonson |
| 6,726,720 | B2 | | 4/2004 | Ross et al. |
| 6,770,095 | B2 | | 8/2004 | Grinberg et al. |
| 6,846,328 | B2 | * | 1/2005 | Cauthen .................... 623/17.11 |
| 2003/0135278 | A1 | * | 7/2003 | Eckman .................... 623/17.14 |
| 2003/0233146 | A1 | * | 12/2003 | Grinberg et al. ........... 623/17.14 |
| 2004/0030387 | A1 | | 2/2004 | Landry et al. |
| 2006/0111783 | A1 | * | 5/2006 | Aflatoon et al. ........... 623/17.14 |

FOREIGN PATENT DOCUMENTS

| | | |
|---|---|---|
| EP | 1374808 | 12/2005 |
| JP | 2003524505 | 8/2003 |
| RU | 2080841 | 6/1997 |
| RU | 2003131308 | 4/2005 |
| WO | 2004041131 | 5/2004 |

\* cited by examiner

*Primary Examiner* — Paul Prebilic
(74) *Attorney, Agent, or Firm* — Simpson & Simpson, PLLC

(57) ABSTRACT

An intervertebral disc prosthesis comprises first and second articulated elements wherein one the elements includes an articulated tongue and the other of the elements includes a groove adapted to receive the tongue. The first and second elements are adapted to be moveable with respect to each other in various planes.

25 Claims, 12 Drawing Sheets

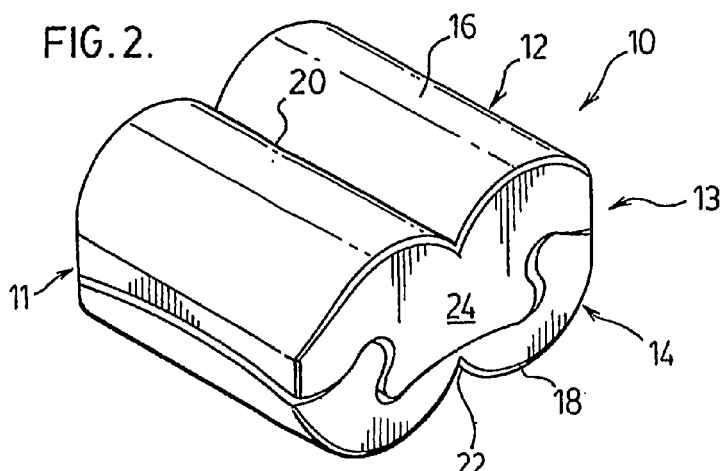
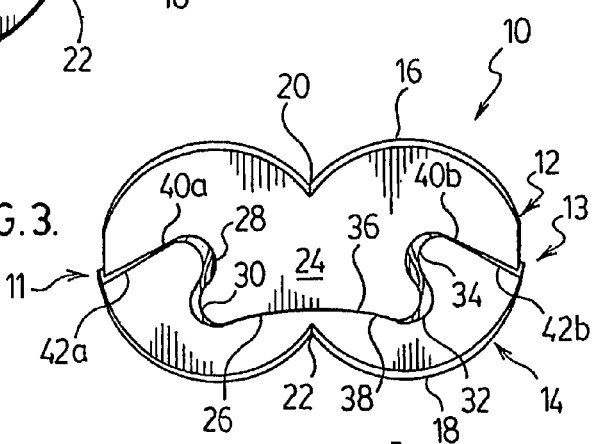
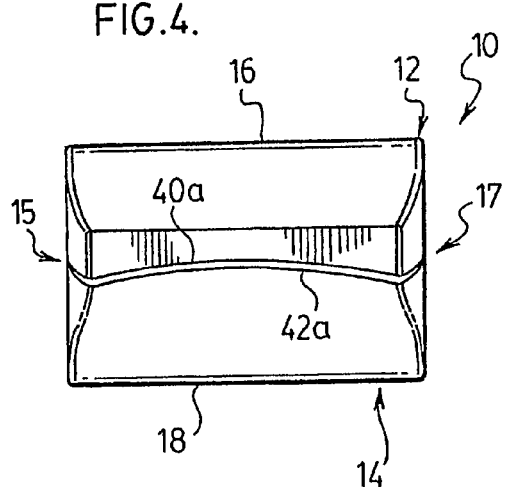
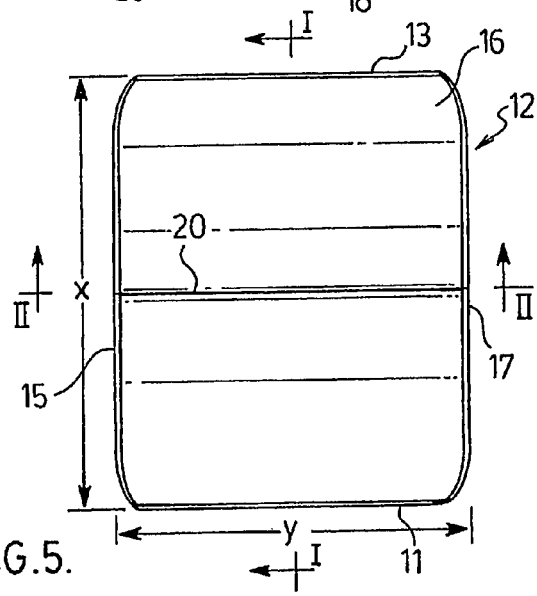

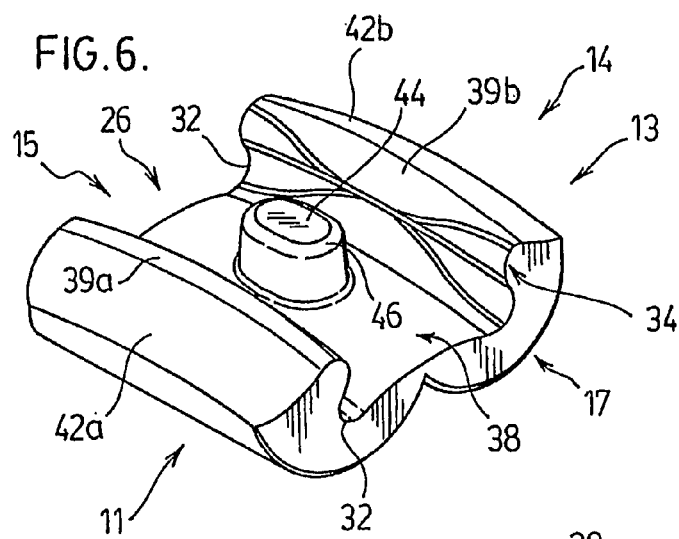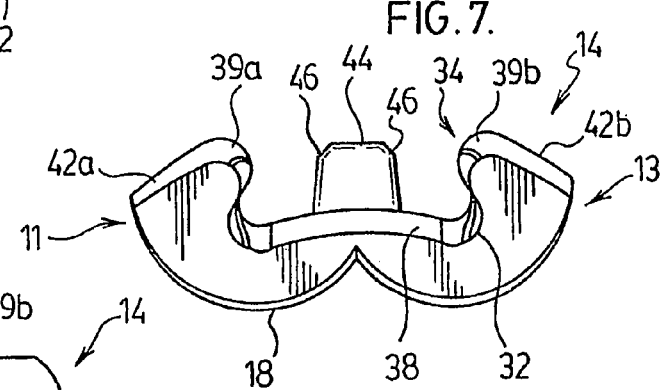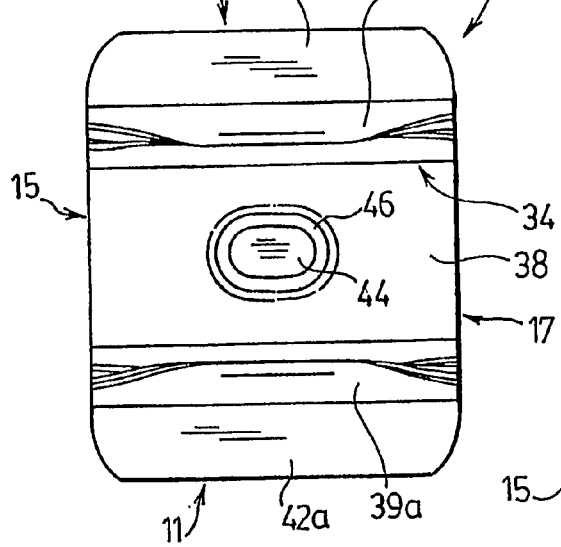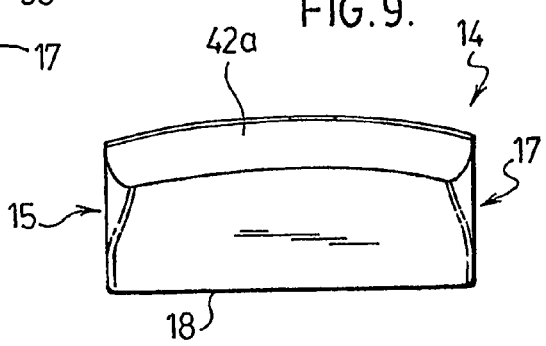

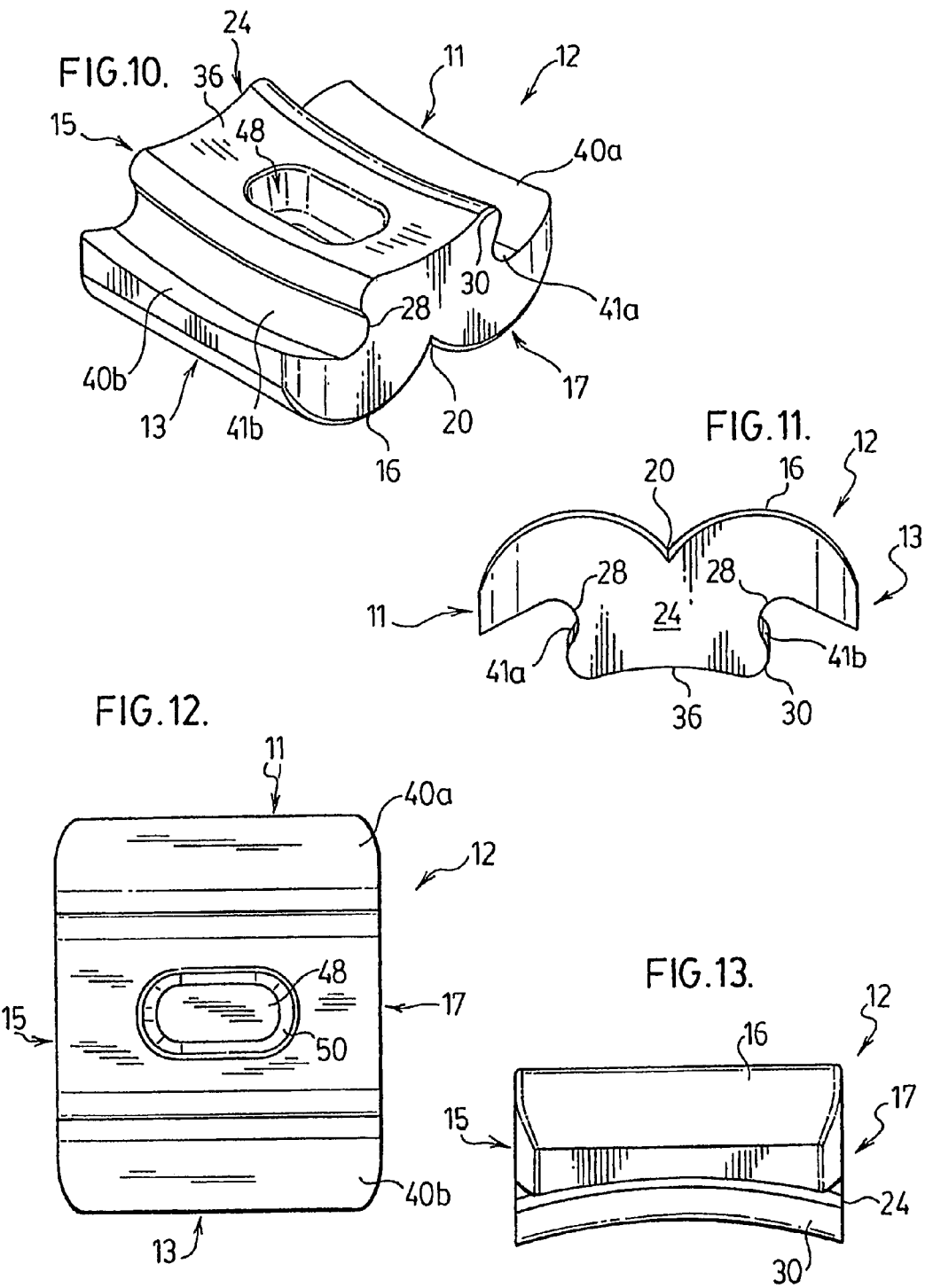

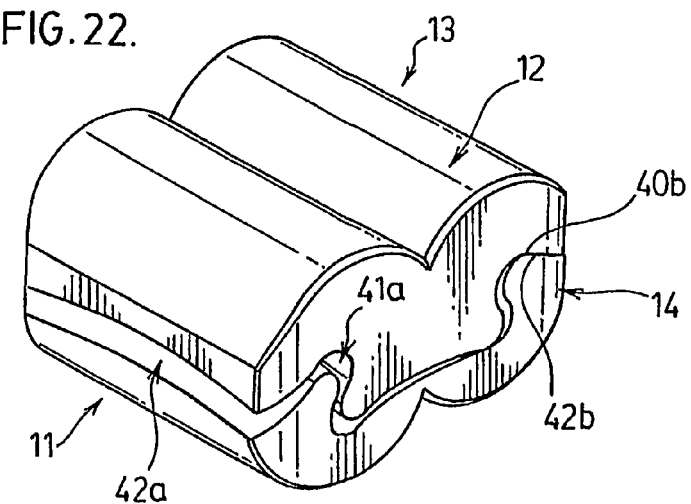
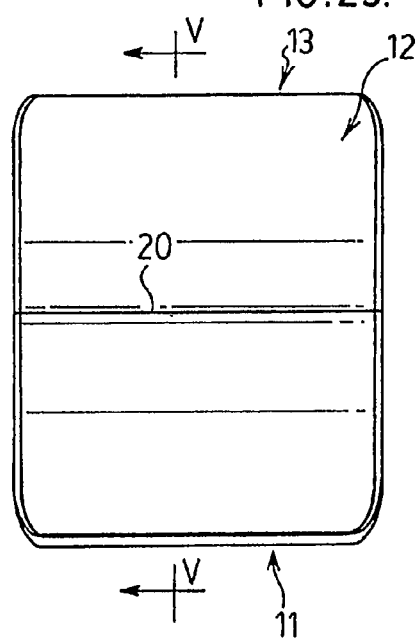
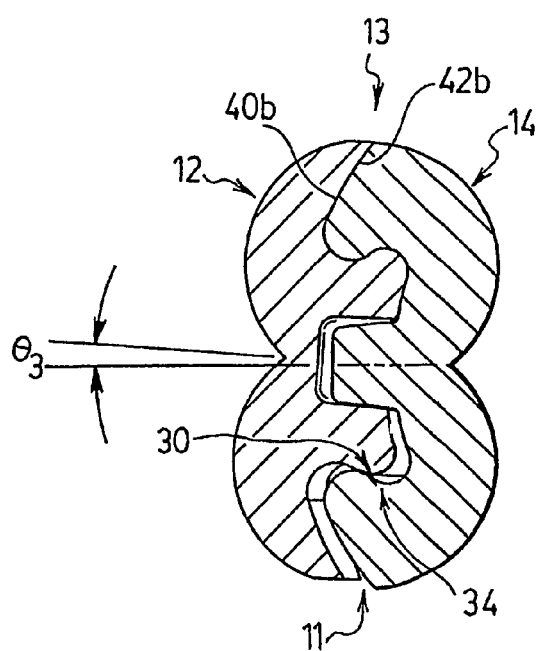

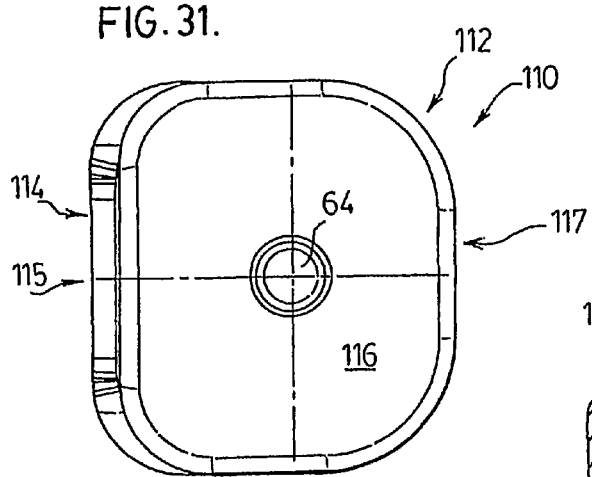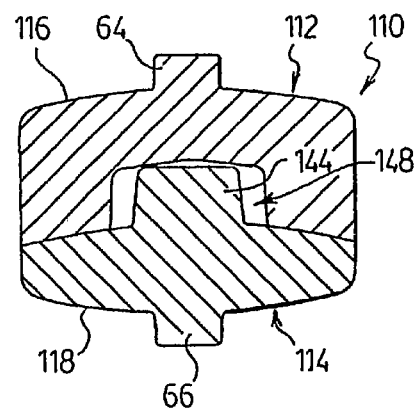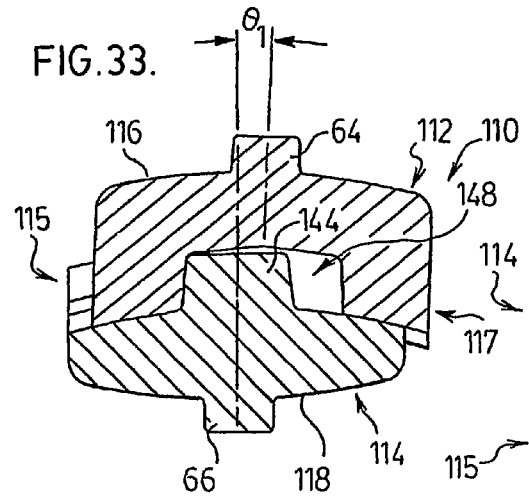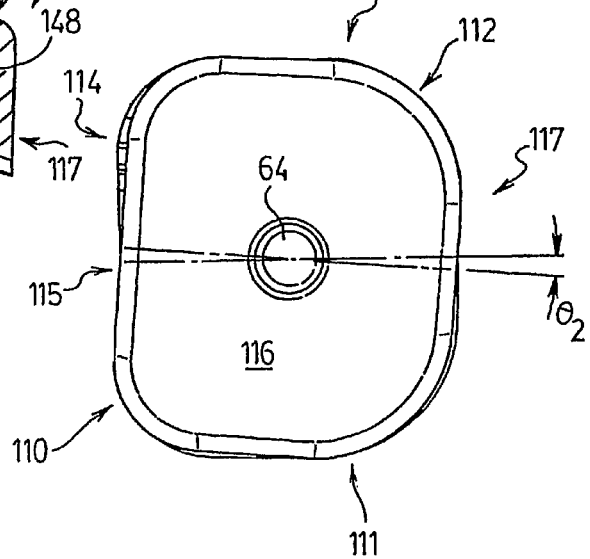

INTERVERTEBRAL DISC PROSTHESIS

CROSS REFERENCE TO PRIOR APPLICATIONS

The present application is a Continuation of PCT application no. PCT/CA2006/000676, filed May 2, 2006, which claims priority from U.S. application No. 60/594,730, filed May 2, 2005. The entire disclosures of these applications are incorporated herein by reference.

FIELD OF THE INVENTION

The present invention relates to the field of artificial joint implants or joint prostheses. In one aspect, the invention relates to spinal implants and, more particularly, to implants comprising intervertebral disc prostheses that provide dynamic spinal stabilisation.

DESCRIPTION OF THE PRIOR ART

The spine is a complicated structure comprised of various anatomical components, which, while being extremely flexible, provides structure and stability for the body. The spine is made up of vertebrae, each having a ventral body of a generally cylindrical shape. Opposed surfaces of adjacent vertebral bodies are connected together and separated by intervertebral discs (or "discs"), comprised of a fibrocartilaginous material. The vertebral bodies are also connected to each other by a complex arrangement of ligaments acting together to limit excessive movement and to provide stability. A stable spine is important for preventing incapacitating pain, progressive deformity and neurological compromise.

The anatomy of the spine allows motion (translation and rotation in a positive and negative direction) to take place without much resistance but as the range of motion reaches the physiological limits, the resistance to motion gradually increases to bring the motion to a gradual and controlled stop.

Intervertebral discs are highly functional and complex structures. They contain a hydrophilic protein substance that is able to attract water thereby increasing its volume. The protein, also called the nucleus pulposis is surrounded and contained by a ligamentous structure called the annulus fibrosis. The main function of the discs is load bearing and motion. Through their weight bearing function, the discs transmit loads from one vertebral body to the next while providing a cushion between adjacent bodies. The discs allow movement to occur between adjacent vertebral bodies but within a limited range thereby giving the spine structure and stiffness.

Due to a number of factors such as age, injury, disease etc., it is often found that intervertebral discs lose their dimensional stability and collapse, shrink, become displaced, or otherwise damaged. It is common for diseased or damaged discs to be replaced with prostheses and various versions of such prostheses, or implants, as are known in the art. One of the known methods involves replacement of a damaged disc with a spacer into the space occupied by the disc. However, such spacers also fuse together the adjacent vertebrae thereby preventing any relational movement there-between.

More recently, disc replacement implants that allow movement between adjacent vertebrae have been proposed. Examples of some prior art implants are provided in the following US patents: U.S. Pat. No. 5,562,738 (Boyd et al.); U.S. Pat. No. 6,179,874 (Cauthen); and U.S. Pat. No. 6,572,653 (Simonson).

Unfortunately, the disc replacement (i.e. implant) solutions taught in the prior art are generally deficient in that they do not take into consideration the unique and physiological function of the spine. For example, many of the known artificial disc implants are unconstrained with respect to the normal physiological range of motion of the spine, in the majority of motion planes. Although some of the prior art devices provide a restricted range of motion, these restrictions are often outside of the normal physiological range of motion; thereby rendering such devices functionally unconstrained. Further, the known unconstrained implants rely on the normal, and in many cases diseased structures such as degenerated facets, to limit excessive motion. This often leads to early facet joint degeneration and other collateral damage to spinal components.

Thus, there exists a need for an intervertebral disc implant that overcomes at least some of the deficiencies in the prior art solutions. More particularly, there exists a need for a spinal implant that allows for the reconstruction of spinal structures while preserving motion and protecting the facet joints of the affected segment of the spine from accelerated degeneration.

SUMMARY OF THE INVENTION

In one aspect, the present invention provides an artificial joint that permits single or coupled motions along various axes within a predetermined range.

In another aspect, the present invention provides an implant for replacing intervertebral discs.

In another aspect, the invention provides an artificial intervertebral disc that allows adjacent vertebrae a range of motion about various axes. Such motion is limited to a predetermined range within which movement of adjacent vertebrae does not lead to deterioration of neighbouring spinal structural components.

In another aspect, above-mentioned motion about various axes can be coupled to more closely simulate natural movement.

BRIEF DESCRIPTION OF THE DRAWINGS

The features of the invention will become more apparent in the following detailed description in which reference is made to the appended drawings wherein:

FIG. 2 is a perspective view of a spinal implant in accordance with one embodiment of the invention.

FIG. 3 is an end view of the implant of FIG. 2.

FIG. 4 is a side view of the implant of FIG. 2.

FIG. 5 is a top view of the implant of FIG. 2.

FIG. 6 is a perspective view of the inferior section of the implant of FIG. 2.

FIG. 7 is an end view of the inferior section of FIG. 6.

FIG. 8 is a top view of the inferior section of FIG. 6.

FIG. 9 is a side view of the inferior section of FIG. 6.

FIG. 10 is a perspective view of the superior section of the implant of FIG. 2.

FIG. 11 is an end view of the inferior section of FIG. 10.

FIG. 12 is a top view of the inferior section of FIG. 10.

FIG. 13 is a side view of the inferior section of FIG. 10.

FIG. 22 is a perspective view of the implant of FIG. 2 when displaced in a side to side direction.

FIG. 23 is a top view of the implant of FIG. 22.

FIG. 24 is a side cross sectional view taken along the line V-V of FIG. 23.

FIG. 31 is a plan view of the implant of FIG. 27 when displaced in an end to end direction.

FIG. 32 is a cross sectional side elevation of the implant of FIG. 29.

FIG. 33 is a cross sectional side elevation of the implant of FIG. 36 in the displaced position of FIG. 31.

FIG. 34 is a plan view of the implant of FIG. 27 when rotationally displaced.

DETAILED DESCRIPTION OF THE INVENTION

The present invention provides artificial discs or implants for replacing intervertebral discs that are damaged or otherwise dysfunctional. The implants of the present invention are designed to preserve motion between adjacent vertebral bodies but with predetermined limitations.

In the following description, the terms "superior", "inferior", "anterior", "posterior", and "lateral" will be used. These terms are meant to describe the orientation of the implants of the invention when positioned in the spine. Thus, "superior" refers to a top portion and "posterior" refers to that portion of the implant (or other spinal components) facing the rear of the body when the spine is in the upright position. It will be appreciated that these positional terms are not intended to limit the invention to any particular orientation but are used to facilitate description of the implant.

Figure 1:
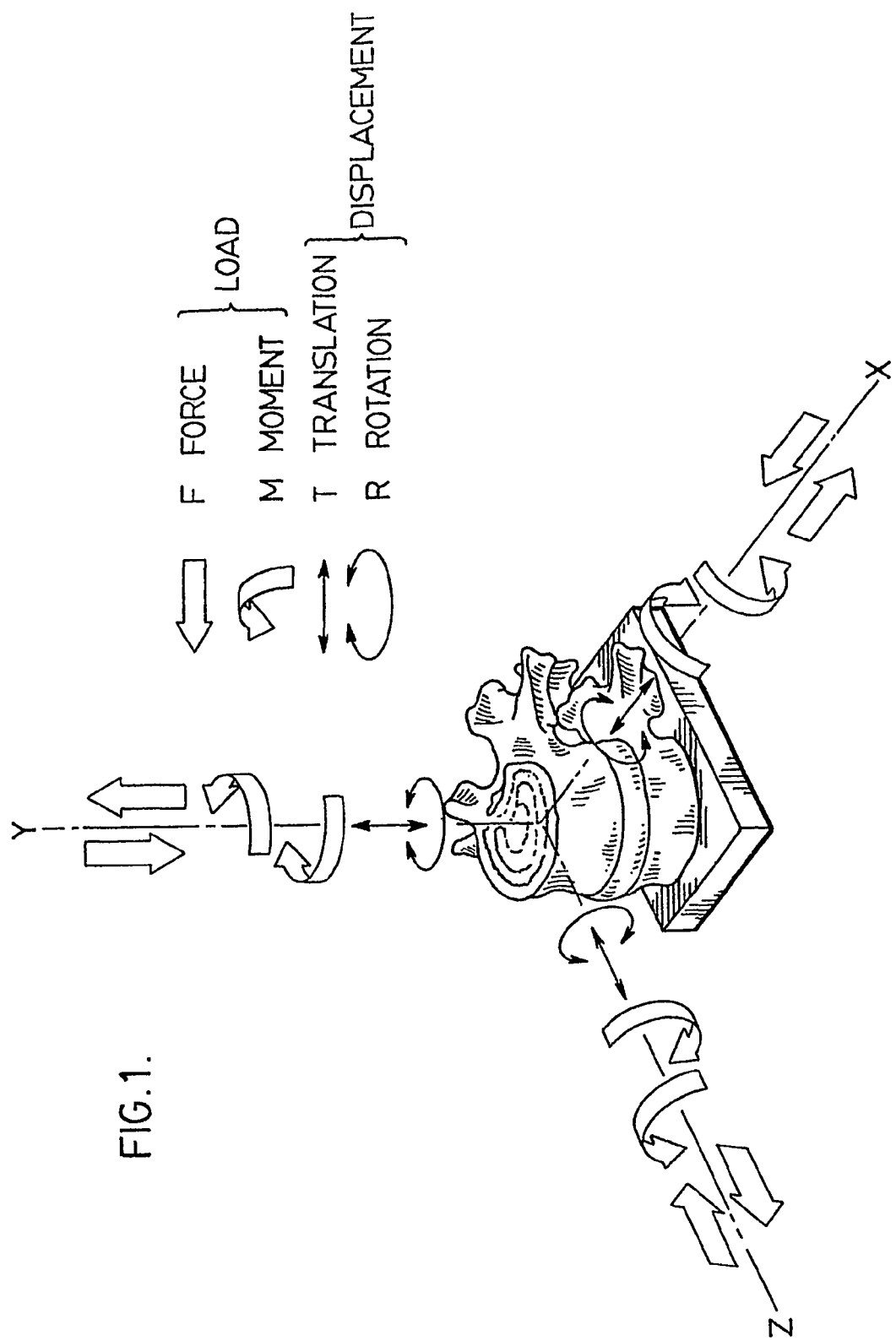
FIG. 1 is a schematic illustration of the range of motion of a vertebra.

FIG. 1 illustrates the complexity of vertebral movement by indicating the various degrees of freedom associated therewith. In the normal range of physiological motion, vertebrae extend between a "neutral zone" and an "elastic zone". The neutral zone is a zone within the total range of motion where the ligaments are relatively non-stressed; that is, the ligaments offer relatively little resistance to movement. The elastic zone is encountered when the movement occurs at or near the limit of the range of motion. At this zone, the visco-elastic nature of the ligaments starts providing resistance to the movement, slowing it down until it stops. The majority of everyday motion occurs within the neutral zone and only occasionally continues into the elastic zone. Motion contained within the neutral zone does not stress soft tissue structures whereas motion into the elastic zone will cause various degrees of elastic responses. Therefore, in the field of spinal implants in particular, by restricting motion to a predetermined zone that mimics the neutral zone, stresses to adjacent osseous and soft tissue structures will be minimised. For example, such limitation of movement will reduce facet joint degeneration.

In general terms, the present invention provides a spinal implant for replacing intervertebral discs. However, because of the unique features of the design, the concept of the invention may also be used to replace, reconstruct or modify other joints and or structures where motion preservation is required. As such, the present invention is not restricted to humans or any particular animal can be used in the spine or elsewhere in the body. The implant of the invention is generally comprised of two sections that are connected by a unique interlocking mechanism and that are moveable relative to each other. Such relative movement includes various degrees of freedom but is limited, by means of a unique combination of stops, to a predetermined specified range depending on the anatomy and functional requirements of the structure it is to replace. In the present disclosure, reference will be made to embodiments of the invention in relation to artificial intervertebral discs. However, it will be understood by persons skilled in the art that, in other embodiments, the present invention can be used to form artificial facet joints, knee joints, hip joints, finger joints etc.

FIG. 2 illustrates an embodiment of the present invention. As shown, the implant 10 includes two sections 12 and 14 that are designed to be interlocked as will be described further below. For convenience, the first section 12 will be referred to as the superior section while the second section 14 will be referred to as the inferior section. It will be understood that these descriptors are not meant to imply any specific arrangement or positioning of the respective sections. Each of the sections 12 and 14 has an outer surface, 16 and 18, respectively. Each of the outer surfaces 16 and 18 are convoluted and include longitudinally extending and generally parallel grooves 20 and 22. As shown in the embodiment of FIG. 2, with sections 12 and 14 combined together, the implant 10 comprises a body having a generally dual cylinder appearance with sides 11 and 13. For convenience, sides 11 and 13 will be referred to as the left side and right side, respectively. However, such description of the sides is not to be considered as limiting the invention, spatially or otherwise, in any way.

FIG. 3 illustrates an end view of the implant of FIG. 2. As can be seen, in the assembled implant, the superior section 12 includes a longitudinally extending tongue 24 that is sized to co-operate with a longitudinally extending groove 26 provided in the inferior section 14. The tongue 24 generally comprises a "T" shaped structure with a waist 28 proximal to the body of the section 12 and a flared end portion 30. The co-operating groove 26 provided in inferior section 14 generally comprises a "U" shape having a base 32 that is wider than the mouth, or opening 34. As shown in the figures, the mouth 34 of the groove 26 is narrower than the flared portion 30 of the tongue 24. However, the base 32 is wider than the flared portion 30. As will be understood, by forming at least the flared portion 30 with a flexible material and forcing the tongue 24 into the groove 26, both the superior and inferior sections 12 and 14 can be locked together by a "snap fit".

Also, according to the embodiment shown FIG. 3, the flared portion 30 of the tongue 24 is sized to be narrower in width (i.e. the dimension taken between the sides 11 and 13) than the base 32 of the groove 26 while, in a similar manner, the waist portion 28 of the tongue 24 is narrower in width than the mouth 34 of the groove 26. Further, the tongue 24 and groove 26 are provided with co-operating concave and convex surfaces 36 and 38, respectively. Both of the surfaces 36 and 38 are sloped between the sides 11 and 13 and the curvatures of same are discussed further below. Thus, as will be understood by persons skilled in the art, the above arrangement allows the superior section 12 to be slidably engaged within inferior section 14 so as to permit the superior section to move between sides 11 and 13 by means of the convex and concave surfaces 36 and 38 sliding over one another. To further facilitate this movement, the contacting surfaces of each of the superior and inferior sections 12 and 14, adjacent to the tongue 24 and groove 26, are provided with sloping edges. More specifically, in the embodiment of the invention shown in FIG. 3, superior section 12 includes two downwardly sloped lateral surfaces or shoulders 40a and 40b, each on opposite sides of the tongue 24. Further, inferior section 14 is also provided with downwardly sloped lateral surfaces or shoulders 42a and 42b, which are positioned to co-operate with surfaces 40a and 40b, respectively. It is understood that the term "downwardly" is used herein for convenience with respect to the orientation of the implant as depicted in FIG. 3 and is not meant to limit the orientation of the implant of the invention in any way. As illustrated, the angles of the sloped surfaces 40a, 40b, 42a and 42b are slightly different thereby resulting in only a portion of the respective surfaces being in contact at any time. Such a relationship serves to gradually limit the range of motion between the respective contact surfaces and, therefore, to limit the respective movement between the sections 12 and 14. This relationship is discussed in more detail below.

As mentioned above, the superior section 12 is designed to move or glide over inferior section 14 so as to permit the section 12 to move towards sides 11 and 13. Further, as can be seen in FIG. 3, the arrangement of the tongue 24 and groove 26, although allowing for some relative movement therebetween, also limit the range of such lateral motion. For example, as can be seen, the superior section 12 can move towards side 11 only until the wall of the mouth 34 of groove 26 contacts the waist 28 of the tongue 24. At such point, any further movement of section 12 in the direction toward side 11 is inhibited. It will be understood that a similar limitation exists with respect to movement towards side 13.

Finally, as also shown in FIG. 3, in one embodiment, the width of the superior section 12, as measured between sides 11 and 13, is slightly narrower than that of inferior section 14. As described herein and as will be understood by persons skilled in the art, this difference in size allows the superior section 12 to "rock" over the inferior section 14 without resulting in the edge of superior section 12 extending over the edge of inferior section 14.

FIG. 4 illustrates the implant 10 from a view of side 11. As shown, the abutting surfaces 40a and 42a of sections 12 and 14, respectively, further include a curve extending between ends 15 and 17 of the implant. For convenience, ends 15 and 17 will be referred to as the rear, or posterior end, and front, or anterior end, respectively. However, such description of the ends is not to be considered as limiting the invention, spatially or otherwise, in any way. It will be understood that the curvatures provided on surfaces 40a and 42a allow for the surface 40a of the superior section 12 to glide across the surface 42a of the inferior section 14. Further, such gliding motion may be described as "rocking".

FIG. 5 illustrates the superior section 12 in a top view. As seen, the section 12, and the implant 10 itself, generally comprises in this embodiment, a rectangular body having a major dimension "X" extending between the sides 11 and 13 and a minor dimension "Y" extending between the ends 15 and 17. In one embodiment, the dimensions of X and Y are 18 mm and 15 mm, respectively. In such embodiment, the height of the implant would be 10 mm. It will be appreciated that the aforementioned dimensions are provided solely for the purpose of assisting the understanding the invention by way of example and are not intended to limit the invention in any way. Various other dimensions of the implant will be apparent to persons skilled in the art.

FIGS. 6 to 9 illustrate various views of the inferior section 14 of the implant of FIG. 2 when not connected to the superior section. As shown, the groove 26 extends longitudinally across the section 14 between ends 15 and 17. As also shown, the convex surface 38 forming the base of the groove 26 includes a further convex curvature extending between the ends 15 and 17 of the section 14. As will be described further below, a corresponding concave curvature is provided on the tongue 24 of superior section 12.

As shown in FIGS. 6 to 8, the inferior section 14 is provided with a peg 44 of a generally oval shape. It will be understood by persons skilled in the art that various other shapes of the peg 44 will be possible. The peg 44 extends from the surface 38 into the groove 26 and is provided generally in the centre of the section 14. In the preferred embodiment, the peg 44 is provided with a tapered upper section 46. The peg 44 is formed preferably integrally with the rest of the section 14. The purpose of the peg 44 will be discussed further below.

In another embodiment, the peg 44 and slot 48 as described could be modified to allow for resistance to compressibility while still allowing for the unique snap lock mechanism to function as designed. This could be achieved through modification of the peg, the slot or both. The peg could be manufactured separately from section 14. It could be manufactured partially or totally from a material that accommodates various degrees of compression such as a hydrogel. A compressible material could be bonded or fixed to a shortened peg to allow for the same overall height and function but with resistance to compression. The base or the end of the peg could also be replaced partially or totally by a coil type mechanism to allow for compression.

The slot 48 could be deepened into section 12 to allow for partial or total filling of the slot with a compressible material such as hydrogel. It is anticipated that the peg would then push against the compressible material within the slot therefore creating resistance to compression. Thus, such resistance will serve to absorb axial forces applied to the disc, particularly when implanted.

Modification of the peg and slot mechanism could involve the creation of a slot 48 into 14 resulting in the creation of slots on both sides. This would create a cavity between 14 and 12 that could be filled with a "block" of compressible material such as hydrogel. It would then function in the same manner as the peg but would be mobile and would move within the "cavity" as the two parts move in relation to each other.

FIGS. 10 to 13 illustrate the superior section 12 of the implant 10. As shown, the curved surface 36 of the tongue 24 is provided with a further radius of curvature extending between the ends 15 and 17 thereby providing the surface 36 with an additional concave structure. As mentioned above, the two radii of curvature of the surface 36 co-operate with same of the surface 38 of the groove 26.

As also shown, particularly in FIGS. 10 and 12, the tongue is provided with a slot 48 that is adapted to receive peg 44 of inferior section 14. The slot 48 is sized to be slightly larger than the peg 44 and, therefore, allows for limited motion in all directions when the peg 44 and slot 48 are in engagement. It will also be understood that, in addition to the other purposes mentioned herein, peg 44 and slot 48 also serve to positively locate the sections 12 and 14 when joining same together.

In reference to FIGS. 6 to 8, it will be seen that the opening of the mouth 34 of the inferior section 14 is defined by opposing tongues 39a and 39b, each extending towards the other, on sides 11 and 13, respectively. Tongues 39a and 39b are opposedly convexly shaped and include a curvature protruding into the mouth 34. Such an arrangement results in the mouth 34 having a narrower gap at the centre of the opening (at the region closest to the peg 44) and a wider gap at the ends 15 and 17. As shown in FIGS. 10 to 12, the waist 28 includes grooves 41a and 41b on sides 11 and 13, respectively. In one embodiment, the grooves 41a and 41b are generally parallel, whereby the waist 28 is provided with a constant width between ends 15 and 17. However, in other embodiments, the grooves may be opposedly convexly shaped so as to provide the waist with a larger width at the centre (at the region closest to the slot 48) and a smaller width at the ends 15 and 17. As will be appreciated from the above description and the accompanying figures, the tongues 39a and 39b are adapted to be received within grooves 41a and 41b, respectively, when the sections 12 and 14 are connected. Further, due to the convex curvature of at least the tongues 39a and 39b, it will be understood that the sections 12 and 14 are thereby permitted to rotate with respect to each other about a central axis. This movement is described further below. In addition, it will be appreciated by persons skilled in the art that by adjusting the radii of curvature of the tongues 39a, 39b and/or the respective grooves 41a, 41b, it will be possible to increase or decrease the permitted range of relative rotation of the sections 12 and 14.

Thus from the above description, it will be appreciated that the specific design and arrangement of co-operating curved surfaces of the superior and inferior sections 12 and 14 provides the following features: (1) A snap-in and locking mechanism for the two sections 12 and 14; and, (2) A soft stop mechanism for limiting the relative movement between the two sections in various directions. Further, it will be appreciated that the co-operating surfaces of the sections 12 and 14 allow for various directional movements to be coupled, or occur simultaneously. For example, the present invention allows the disc to couple movements associated with flexion, lateral rotation and lateral bending. As indicated above, these ranges of motion are defined in relation to one aspect of the invention wherein the implant comprises an artificial intervertebral disc. It will therefore be understood that for other joints, all degrees of freedom of movement associated with spinal joints may not be necessary. For example, with respect to finger joints, movement in a single plane may suffice.

Firstly, as described above, the superior and inferior sections are snapped together by contacting the facing surfaces of the sections 12 and 14 so as to introduce the tongue 24 into the groove 26. Locking of the two sections together is achieved by forcing the tongue into the groove so as to form a "snap" fit. The snap-in mechanism is created by forming the waist 28 of tongue 24 of the superior section 12 to be slightly wider than the mouth 34 of the groove 26 of the inferior section 14 so that a small force is needed to force the tongue into the groove. It will be understood that such snap fit will only occur when the peg 44 and slot 48 are aligned so as to allow the peg 44 to enter into the slot 48. The sections are preferably designed so that that once snapped together, it is extremely difficult to separate them. The snap-in tongue and groove mechanism results in a variable semi-constrained motion between the two abutting sections 12 and 14. It will be understood that the mechanism allows for motion yet at the same time it also restricts excessive motion beyond a variable predetermined range. Further, as discussed above, by sizing the slot 48 of the superior section 12 to be slightly larger than the peg 44 of the inferior section 14 prevents motion from taking place beyond the constraints imposed by the peg and slot in all planes of motion beyond a predetermined range. The predetermined range in both cases will preferably be limited to motion within the predetermined range as described above.

Secondly, with respect to the "soft stop" mechanism of the invention, as explained above, the articular abutting surfaces of each of the sections 12 and 14 (i.e. surfaces 36 and 38, 40a and 42a, 40b and 42b) are shaped and optimised for smooth articulation to minimise wear in designated areas but in other areas the articular surfaces are optimised to increase resistance to motion forming a soft stop mechanism. The soft stop mechanism is created by the arranging the convex and concave surfaces making up the articular sides of both the superior and inferior endplates. Specifically, the radius of curvature of the respective convex and concave surfaces of the invention changes with respect to each other as the two sections 12 and 14 move in relation to each other. In this regard, the convex surfaces of the implant are preferably provided with a lesser radius of curvature than the counterpart concave surfaces. In this manner, as the convex surface slides along the concave surface, the resistance to motion is at first minimal, then as the range of motion increases away from the neutral zone the resistance to motion gradually increases. This arrangement is referred to herein as a "soft stop". As the resistance increases, the ease of motion decreases but if the motion would continue to increase the "hard stop" (i.e. when, for example, the wall of the tongue 24 contacts the wall of the groove 26) would be reached. This can be explained as resistance to uphill motion as the convex surface slides uphill along the concave surface. The gradual increase in resistance results in a "buffer zone" being created before the hard stop is reached. This buffer zone in the total range of motion protects the fusion/fixation surface from sudden shear forces that are associated with prior art implants that have low resistance to motion and a sudden hard stop. Thus, by creating such a "buffer zone", the present invention protects the adjacent soft tissue from excessive stresses as the stop is built into the design of the device and does not depend on normally functioning structures or partially diseased structures such as ligaments or facet joints.

Due to the nature of the locking mechanism and the soft stop, the implant of the present invention has the ability to function independently of the facet joints of adjacent vertebrae since the functions of the paired facet joints are built into the implant design itself. The implant of the invention can thus provide stability to the spine even in the absence of the posterior elements. This makes the invention extremely useful in certain applications such as trauma or in other cases of instability.

It will be understood that the discs of the invention can be implanted in various regions of the spine including cervical, thoracic and lumbar.

The relative movement of the sections 12 and 14 will now be described with reference to the following Figures.

Neutral Position

Figure 14:
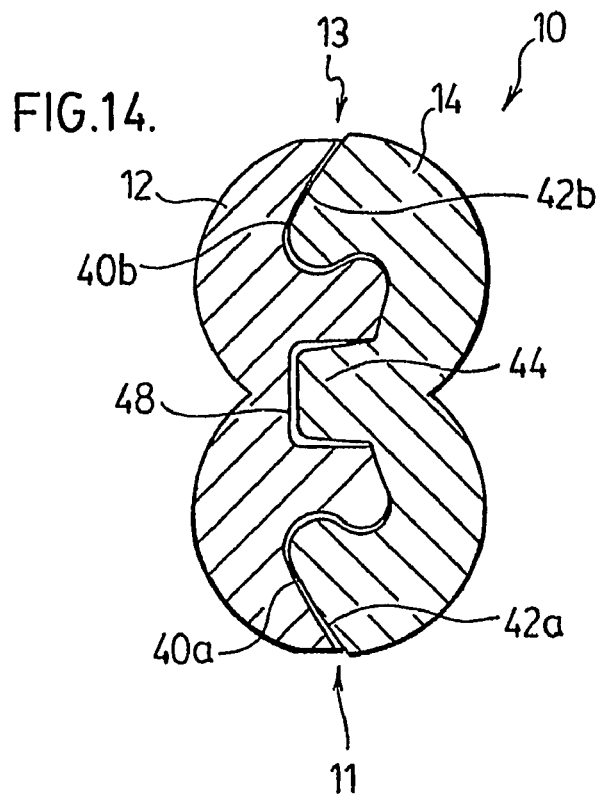
FIG. 14 is an end cross sectional view taken along the line I-I of FIG. 5.
Figure 15:
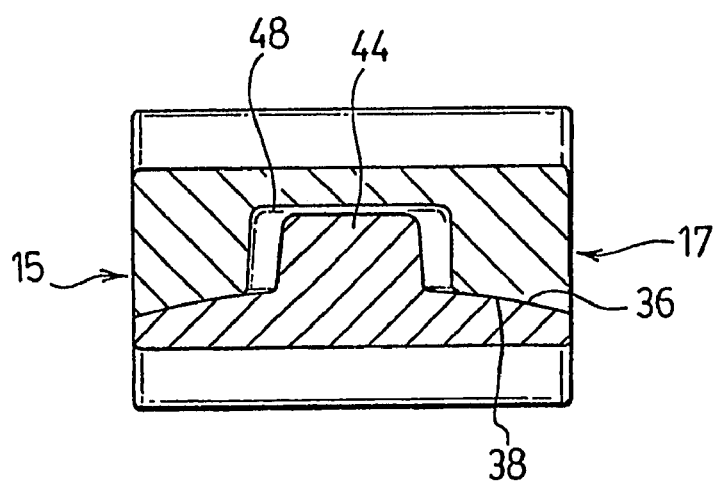
FIG. 15 is a side cross sectional view taken along the line II-II of FIG. 5.

FIGS. 14 and 15 are cross sectional views of the implant of FIG. 5 taken along the planes I-I and II-II, respectively. As can be seen, both the sections 12 and 14 are aligned when the implant is in the neutral position. FIG. 14 also illustrates the difference in the radii of curvature of the various co-operating curved surfaces of the sections 12 and 14 by showing that only certain portions of the opposing surfaces are in contact. FIGS. 14 and 15 also illustrate the size difference between the peg 44 and the slot 48. As shown, and as will become clearer in the following description, the slot has a larger size difference along its length, that is, the dimension when measured between the ends 15 and 17.

1) Flexion and Extension

Figure 16:
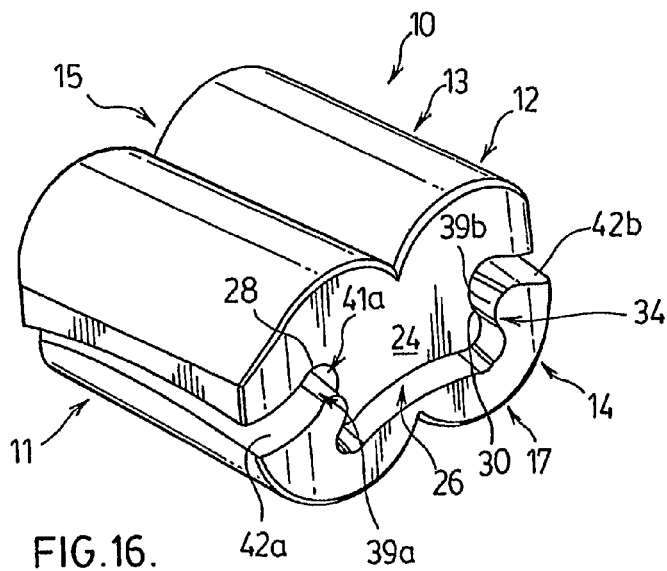
FIG. 16 is a perspective view of the implant of FIG. 2 when displaced in an end to end direction.
Figure 17:
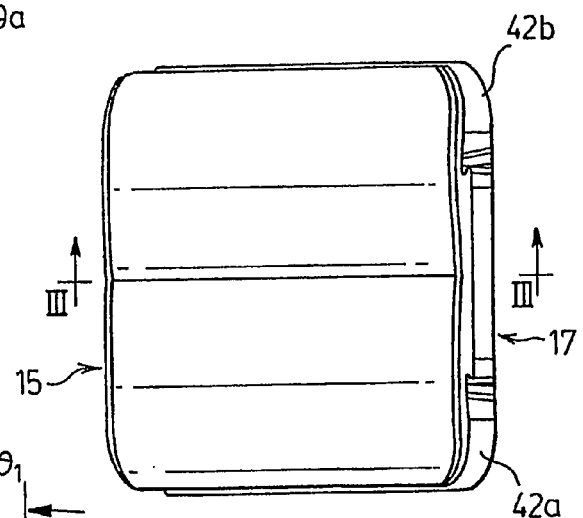
FIG. 17 is a top view of the implant of FIG. 16.
Figure 18:
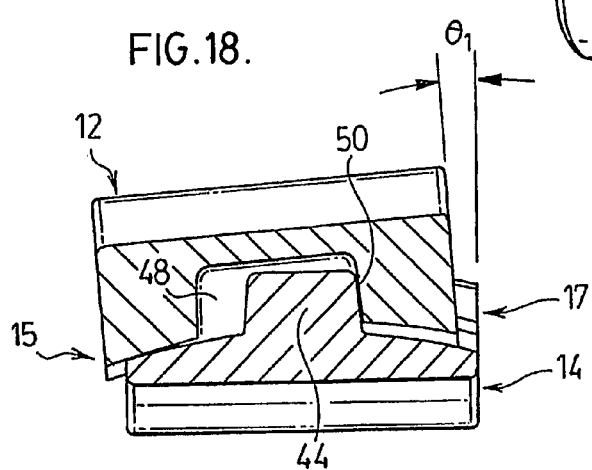
FIG. 18 is a side cross sectional view taken along the line III-III of FIG. 17.

FIGS. 16 to 18 illustrate the implant 10 of FIG. 2 when displaced in an end to end manner, that is, one of the sections, for example superior section 12, is moved toward one of ends 15 or 17 with respect to the other section, for example inferior section 14. Such displacement would occur when the spinal region containing the implant is moved in either a posterior to anterior (flexion) or anterior to posterior (extension) direction. As can be noted, the range of motion between the superior 12 and inferior 14 sections of the implant are limited in two ways. First, in the course of a movement wherein the superior section 12 is moved toward the posterior end 15, the flared portion 30 of the tongue 24, at the front end 17 rises upwardly to contact the wall of the mouth 34 of the groove 26 of the inferior section 14. This restriction to movement is illustrated in FIG. 16. Further, as illustrated in FIG. 18, movement of the superior section towards the posterior end 15 is continued until the front wall 50 of the slot contacts the peg 44 at which point, further movement is hindered. As also noted in FIG. 18, movement of the superior section 12 is continued until the end wall of the section is offset by an angle of displacement $\theta_1$. In one embodiment, this angle of displacement may be 4.25° for each direction. Thus, for a complete range of flexion and extension, the range of movement offered by the implant would be 8.5°. It will be understood that this range is simply an example and should not be considered as limiting the invention in any way.

2) Rotation

Figure 19:
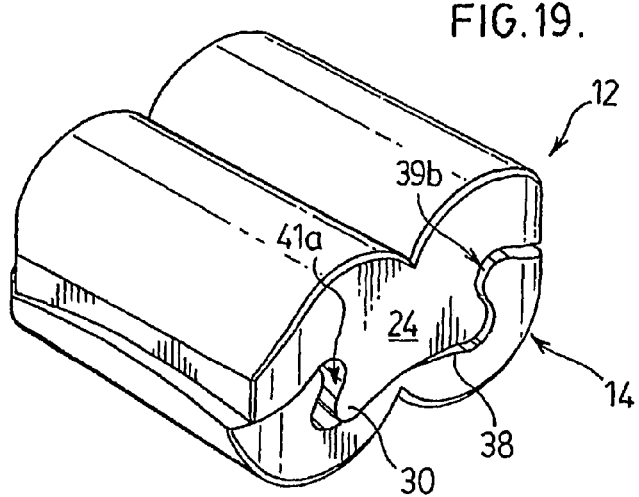
FIG. 19 is a perspective view of the implant of FIG. 2 when rotationally displaced.
Figure 20:
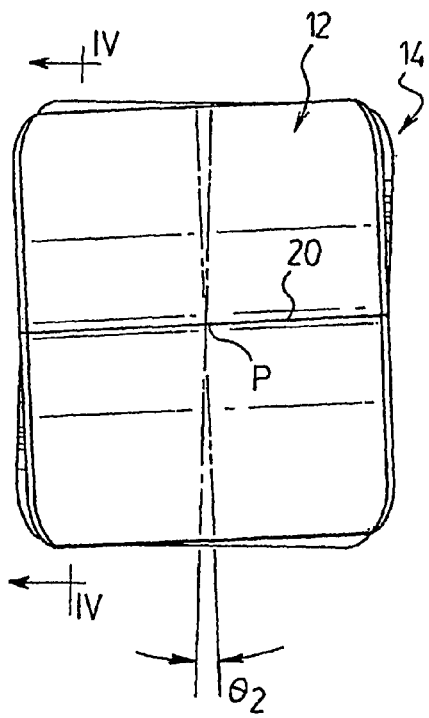
FIG. 20 is a top view of the implant of FIG. 19.
Figure 21:
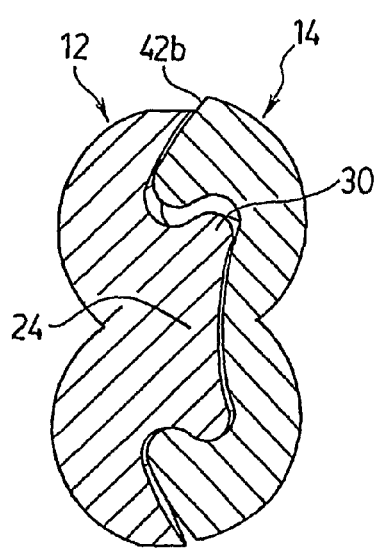
FIG. 21 is a side cross sectional view taken along the line IV-IV of FIG. 20.

FIGS. 19 to 21 illustrate the implant of the invention when the superior section 12 is axially rotated with respect to inferior section 14 about a vertical axis. The term "vertical" is used as a matter of convenience and should not be considered as limiting the invention to any particular spatial orientation. As shown in FIGS. 19 and 21, the rotational movement of the superior section 12 is limited at the point where the ends of the tongues 39a (not shown) and 39b (shown) contact with the ends of the grooves 41a (shown) and 41b (not shown), respectively. Rotation of the superior section 12 about a central axis point P can be permitted up to an angle $\theta_2$. As will be understood in light of the foregoing description, axis point P lies essentially in the centre of the disc by virtue of the convex shape of the tongues 39a and 39b. As discussed above, the relative sizing of the various movement limiting components will be apparent to persons skilled in the art upon reviewing the present disclosure. By way of example, the sizing of the components can be made to permit an angle of rotation ($\theta_2$) of 4° in one direction. Thus, the total range of axial rotation offered by the implant would be 8°. It will be understood that this range is simply an example and should not be considered as limiting the invention in any way.

3) Lateral Bending

FIGS. 22 to 24 illustrate movement of the superior section 12 of the implant in a side to side or lateral flexion motion. By side to side or lateral flexion, it is meant a direction of the motion wherein the superior section 12 is moved laterally towards the right side 13 of the implant. As will be understood, the section 12 can be moved towards the left side 11 as well. In the example shown in FIGS. 22 and 24, it is noted that movement of the superior section 12 is restricted when the flared portion 30 on the left side of the tongue 24 abuts the wall of the mouth 34. It is also noted that such restriction occurs by surface 40b of the superior section 12 abutting surface 42b of the inferior section 14. The movement of the superior section 12 can be permitted to continue over an angle $\theta_3$ of, for example, 4° in each direction. Thus, the total range of motion for lateral motion offered by the implant would be 8°. It will be understood that this range is simply an example and should not be considered as limiting the invention in any way.

Other Embodiments

In other aspects of the invention, the outer or fusion surfaces 16 and 18 of sections 12 and 14 can be treated for promoting osseous in-growth or can be shaped to promote fixation of the implant to adjacent bone structures. Various methods of surface preparation can be employed to enhance the osteoconductive properties of the implant for solid integration with adjacent bone. For example, different coatings with plasma, titanium or hydroxyapatite etc. may be used. Further, the implant may be provided with holes or micro pores, spikes or pins as well as other features to promote fixing to adjacent bone structures.

Figure 25:
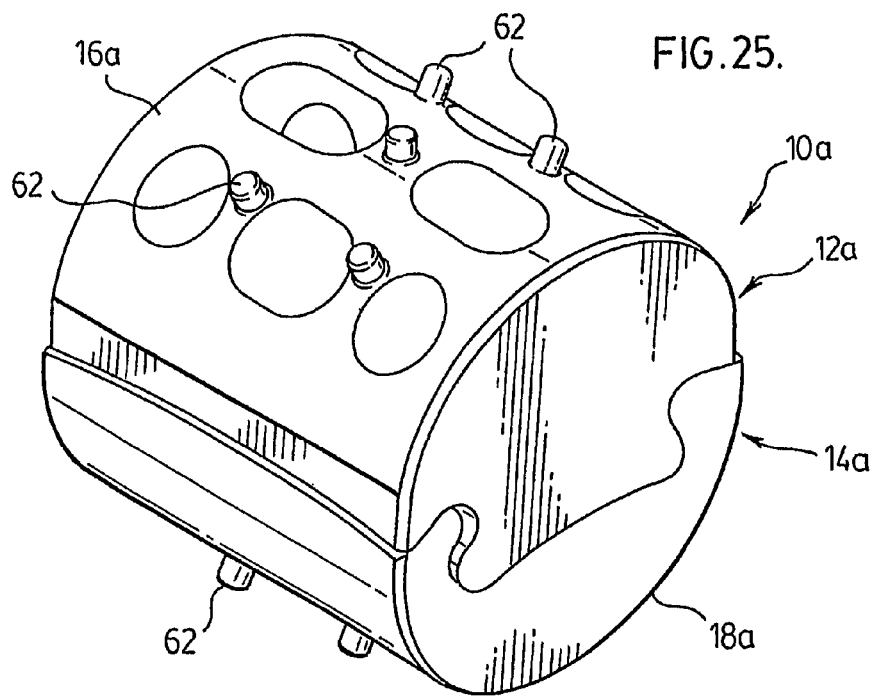
FIG. 25 is a perspective view of an implant in accordance with another embodiment of the invention.
Figure 26:
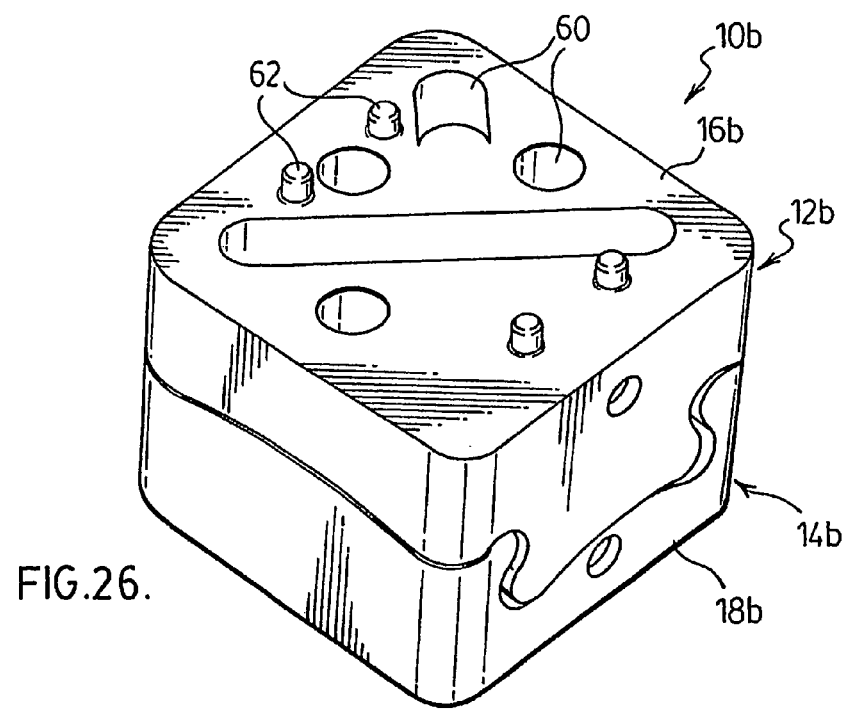
FIG. 26 is a perspective view of an implant in accordance with another embodiment of the invention.

FIGS. 25 and 26 illustrate other possible embodiments of the invention. FIG. 25 illustrates a "single dowel" design wherein the implant 10a has a generally cylindrical shape. The implant 10a is comprised of superior and inferior sections 12a and 14a as with the embodiment discussed above and includes all similar features. Also illustrated in FIG. 25 are various holes 60 and spikes 62 that may be provided on the outer surfaces 16a and 18a of the superior and inferior sections, respectively. As discussed above, the holes 60 and spikes 62 serve to facilitate or promote bone in-growth thereby serving to anchor the implant 10a FIG. 26 illustrates at 10b another embodiment of the implant of the invention wherein the implant is provided in a generally rectangular shape, having superior and inferior sections 12b and 14b, respectively. As with the previous figure, the outer surfaces 16b and 18b of the sections 12b and 14b may be provided with a plurality of holes 60 and spikes 62.

A further embodiment of the invention is illustrated in FIGS. 27 to 37, wherein elements equivalent to those described above are shown with the same reference numerals but with the prefix "1" for convenience. As shown, the artificial disc or implant 110 includes a superior section 112 and an inferior section 114, each having respective outer surfaces 116 and 118 (forming, respectively, the top and bottom surfaces of the implant, when implanted in the spine). As with the previous embodiment, the superior section 112 includes a tongue 124 that is adapted to be received within a groove 126 in the inferior section 114. The disc 110 includes a front or anterior end 117 and a posterior end 115 and left and right sides 111 and 113, respectively. The embodiment of FIGS. 27 to 37 is preferably used to replace intervertebral discs in the cervical section of the spine; however, it will be understood that the disc may equally be implanted in other sections of the spine (i.e. thoracic or lumbar).

In the embodiment shown in FIGS. 27 to 30, the top and bottom surfaces 116, 118 are provided with tabs 64 and 66, respectively. In one aspect, the tabs 64 and 66 are generally cylindrically shaped protuberances extending from each of surfaces 116 and 118 in a direction generally normal to such surfaces. Tabs 64 and 66 serve to anchor the disc 110 when implanted, wherein the tabs are implanted within the vertebrae. It will be understood that the tabs and/or other surfaces of the disc may be provided with texture or coatings etc. to enhance the securing of the implant to the adjacent indigenous structures. In general, the outer surfaces 116 and 118 may be provide with one or more bone anchoring means such as physical or chemical anchoring means. For example, the physical bone anchoring means may comprise pegs, pins, pores or apertures and the chemical anchoring means may comprise adhesives or tissue growth promoters.

Figure 30:
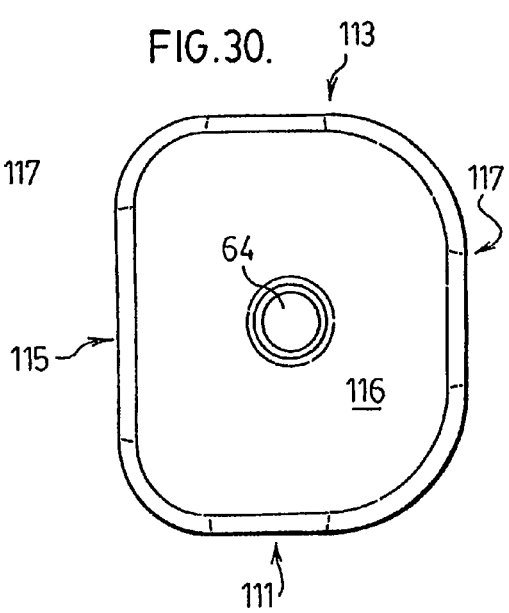
FIG. 30 is a plan view of the implant of FIG. 27.

As illustrated particularly in FIG. 30, the disc 110 is provided, in one aspect, with a generally square "footprint". Further, in a preferred aspect, the posterior end 115 of the disc 110 may have a greater width (i.e. the dimension between sides 111 and 113) than the anterior end 117. This may be achieved by, as shown in FIG. 30, rounding the corners of the anterior end 117. Such a geometry serves to conform the disc 110 to the generally asymmetrical vertebrae to which the disc is to be connected. In this manner, the surface area of the disc 110 contacting bone tissue of adjacent vertebrae is maximised thereby maximising the degree of bone in-growth into the disc. As will also be appreciated by persons skilled in the art, maximising contact of the disc 110 with adjacent bone surfaces serves to minimise or prevent the settlement of the disc within softer tissues of the vertebrae. In the latter case, it will be appreciated that the minimisation of such "settling" preserves the height of the vertebrae/disc complex after implantation.

FIGS. 27 to 30 illustrate the disc of the invention in the neutral position. The following figures will illustrate the disc when displaced. As can be seen in FIGS. 31 to 37, and as described further below, the embodiment of the invention shown in these figures includes the same "stop" mechanisms as discussed above.

FIG. 31 illustrates the disc of FIG. 30 when displaced anteriorly in the sagittal plane. That is, the superior section 112 is moved anteriorly (i.e. towards end 117) with respect to the inferior section 114. This movement can be more clearly seen in comparing FIGS. 32 and 33. FIG. 32 illustrates a cross sectional side elevation of the disc 110 in the neutral position whereas FIG. 33 illustrates the disc in the displaced position of FIG. 31. FIGS. 32 and 33 also illustrate the peg 144 and the corresponding slot 148 of the disc, which combine to provide one of the "stops" for the above movement. As illustrated in the figures, the superior section 112 is permitted a movement up to a point where the central axis of the section is moved across an angle $\theta_1$, which is the same range of movement of the embodiment discussed above. In one embodiment, the angle $\theta_1$ is 4.25°, thereby allowing a range of motion of 8.5°.

Figure 27:
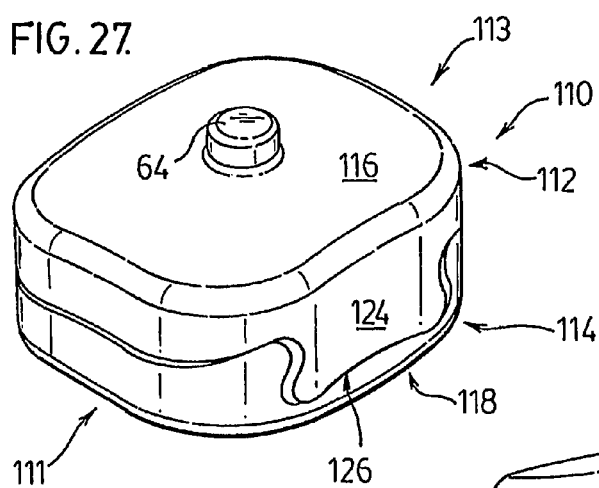
FIG. 27 is a perspective view of an implant in accordance with another embodiment of the invention.
Figure 28:
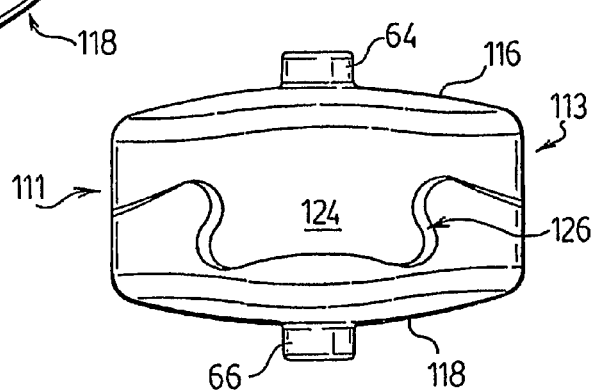
FIG. 28 is a front view of the implant of FIG. 27.
Figure 29:
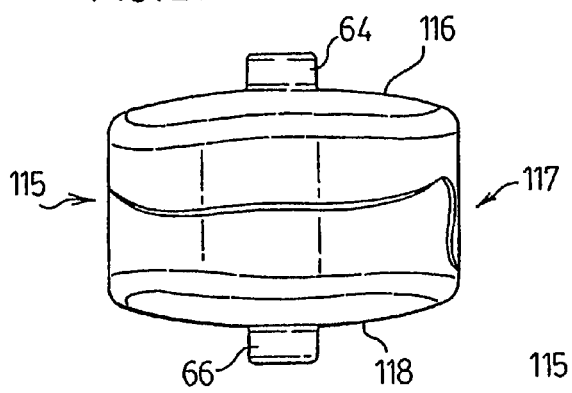
FIG. 29 is a side view of the implant of FIG. 27.

FIG. 34 illustrates a plan view of the embodiment of FIG. 27 when rotationally displaced about a central axis. FIG. 34 shows superior section 112 rotated with respect to inferior section 114 in the direction towards side 111. The various "stops" provided on the disc, which are essentially the same as those discussed above, allow one of the sections to rotate about an angle of $\theta_2$. This angle, as with the previous embodiment, may be 4° in each direction, thereby providing a rotational range of 8°.

Figure 35:
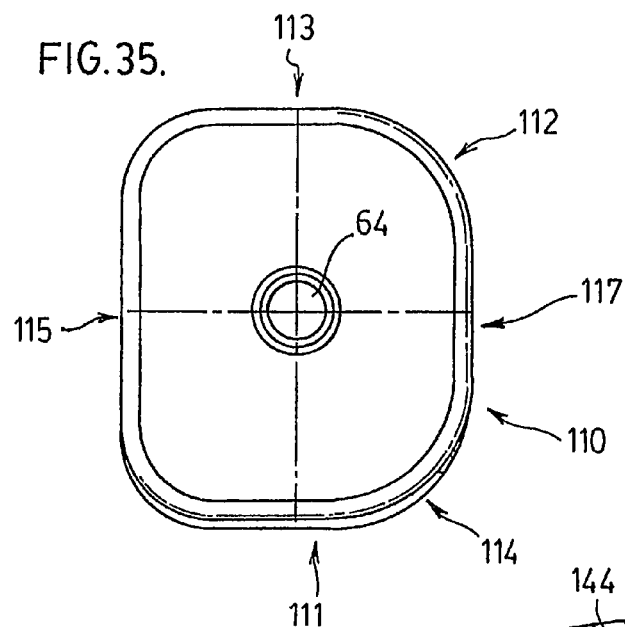
FIG. 35 is a plan view of the implant of FIG. 27 when displaced in a side to side direction.
Figure 36:
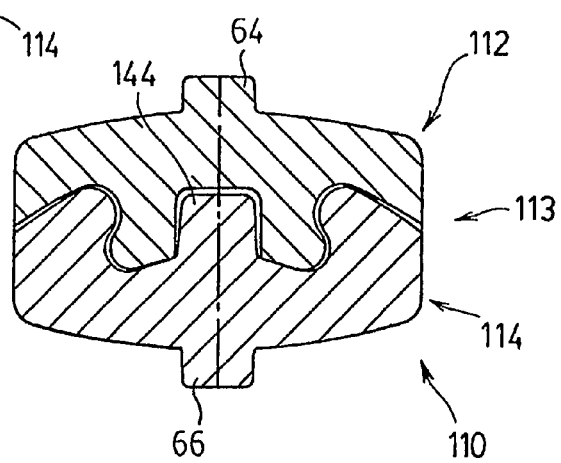
FIG. 36 is a cross sectional side elevation of the implant of FIG. 28.
Figure 37:
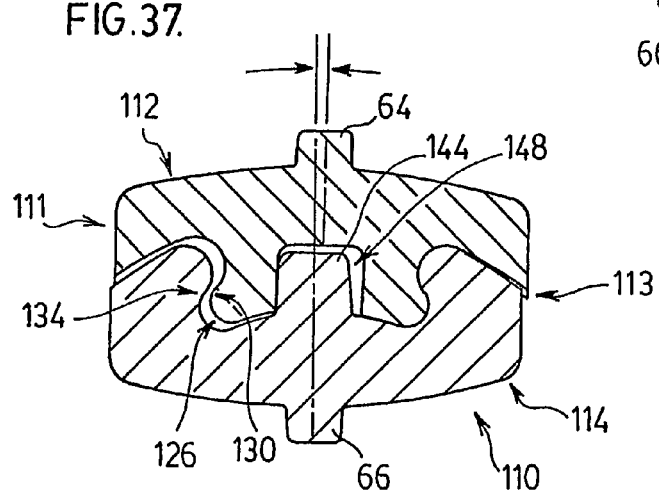
FIG. 37 is a cross sectional front elevation of the implant of FIG. 36 is the displaced position of FIG. 35.

FIG. 35 illustrates the disc of FIG. 27 when displaced in a side to side direction (i.e. in the coronal plane), and more specifically, wherein the superior section 112 is displaced towards the right side 113 with respect to inferior section 114. FIG. 36 illustrates a front cross sectional elevation of the disc 110 in the neutral position while FIG. 37 illustrates the disc in the displaced position of FIG. 35. As shown, the superior section 112 is permitted to travel to a point where its central axis is offset by an angle $\theta_3$ with such movement being limited in the same manner as with the embodiment discussed above. In one embodiment, the angle $\theta_3$ is 4°, thereby allowing a range of movement of 8° in the coronal plane. As with the previous embodiment, the range of motion of the section 112 in the coronal plane is limited by the flared portion 130 contacting the mouth 134 of the groove 126.

The various embodiments of the invention have been described with reference to implantation in the spine as replacements for intervertebral discs. However, it will be understood by persons skilled in the art that the implants (or discs) of the invention will find applications in various other joint regions of the body.

Although the invention has been described with reference to certain specific embodiments, various modifications thereof will be apparent to those skilled in the art without departing from the purpose and scope of the invention as outlined herein. The entire disclosures of all references recited above are incorporated herein by reference.

We claim:

1. An intervertebral disc prosthesis comprising:
   first and second cooperating elements, said elements having anterior and posterior ends and lateral sides;
   the first element including an outer surface and an inner surface directed towards the second element;
   the second element including an outer surface and an inner surface directed towards the first element;
   the first element inner surface including a generally central, longitudinally extending articulated tongue extending between the anterior and posterior ends of the first element, and a first pair of articulated shoulders extending longitudinally on opposite sides of said tongue;
   the second element inner surface including a generally central, longitudinally extending articulated groove extending between the anterior and posterior ends of the second element, and a second pair of articulated shoulders extending longitudinally on opposite sides of said groove;
   the tongue and groove being generally complementary in shape whereby, when the prosthesis is in an assembled state, the groove is adapted to moveably receive the tongue therein;
   the first and second pairs of shoulders being in cooperative arrangement wherein the shoulders of the first element bear against the shoulders of the second element when the prosthesis is in the assembled state;
   said tongue comprising a proximal end, proximal to the inner surface of the first element, and a terminal end opposite the first end, wherein the proximal end has a narrower width, in transverse cross section, than the terminal end;
   said groove defined by an opening, opposed side walls, and a base for accommodating the tongue terminal end, the opening of the groove being narrower, in transverse cross section, than the width of the terminal end of the tongue;
   and wherein the opening of the groove includes opposing tongues extending from the upper edges of the side walls opposite to the base and longitudinally across the second element, wherein the tongues define a narrowed region of the opening, generally centrally along the length of the groove.

2. The prosthesis of claim 1, wherein the terminal end of said tongue and the base of said groove include a cooperating articulation for allowing relative translational movement of the first and second elements between the anterior and posterior ends and for allowing relative lateral movement of the first and second elements.

3. The prosthesis of claim 2 wherein the difference in size between the terminal end of the tongue and the opening of the groove limits the amount of said translational and lateral movement, wherein said movement is restricted when the tongue terminal end contacts the opening of the groove.

4. The prosthesis of claim 1, wherein the base of said groove is wider than the terminal end of the tongue for allowing relative axial rotation between the first and second elements.

5. The prosthesis of claim 4 wherein the difference in size between the base of said groove and the terminal end of the tongue limits the amount of said rotational movement, wherein said movement is restricted when the tongue terminal end contacts the wall forming the base of the groove.

6. The prosthesis of claim 1, wherein one of said first and second elements includes a generally centrally located peg extending from the inner surface thereof and wherein the other of said first and second elements includes a recess for receiving said peg.

7. The prosthesis of claim 6, wherein said recess is larger than said peg.

8. The prosthesis of claim 1, wherein one of the first and second shoulders comprise convexly shaped surfaces and the other of the first and second shoulders comprise concavely shaped surfaces and wherein the first and second shoulders bear against each other over the respective convexly and concavely shaped surfaces.

9. The prosthesis of claim 7, wherein contact of said peg with the wall of said recess limits relative movement between the first and second elements.

10. The prosthesis of claim 6, wherein said recess comprises a base containing resilient material.

11. The prosthesis of claim 6, wherein said peg is provided on the second element and said recess is provided on the first element.

12. The prosthesis of claim 1, wherein the outer surfaces of the first and second elements are provided with one or more bone anchoring means.

13. The prosthesis of claim 12, wherein said bone anchoring means comprises one or more physical and chemical anchoring means.

14. The prosthesis of claim 13, wherein said bone anchoring means are chosen from pegs, pins, pores, apertures, adhesives, and tissue growth promoters.

15. The prosthesis of claim 1, wherein the outer surfaces of the first and second elements are generally convex about the transverse plane perpendicular to the anterior-posterior axis thereof.

16. The prosthesis of claim 1, wherein the outer surfaces of the first and second elements are provided with a groove extending along the anterior-posterior axis thereof.

17. The prosthesis of claim 1, wherein the outer surfaces of the first and second elements are generally planar.

18. An intervertebral disc prosthesis comprising:
first and second cooperating elements, said elements having anterior and posterior ends and lateral sides;
the first element including an outer surface and an inner surface directed towards the second element;
the second element including an outer surface and an inner surface directed towards the first element;
the first element inner surface including a generally central, longitudinally extending articulated tongue extending between the anterior and posterior ends of the first element, and a first pair of articulated shoulders extending longitudinally on opposite sides of said tongue;
the second element inner surface including a generally central, longitudinally extending articulated groove extending between the anterior and posterior ends of the second element, and a second pair of articulated shoulders extending longitudinally on opposite sides of said groove;
the tongue and groove being generally complementary in shape whereby, when the prosthesis is in an assembled state, the groove is adapted to moveably receive the tongue therein;
the first and second pairs of shoulders being in cooperative arrangement wherein the shoulders of the first element bear against the shoulders of the second element when the prosthesis is in the assembled state;
wherein one of said first and second elements includes a generally centrally located peg extending from the inner surface thereof and wherein the other of said first and second elements includes a recess for receiving said peg.

19. The prosthesis of claim 18, wherein:
said tongue includes a proximal end, proximal to the inner surface of the first element, and a terminal end opposite the first end, wherein the proximal end has a narrower width, in transverse cross section, than the terminal end; and,
said groove comprises an opening and a base for accommodating the tongue terminal end, the opening of the groove being narrower, in transverse cross section, than the width of the terminal end of the tongue.

20. The prosthesis of claim 19, wherein the terminal end of said tongue and the base of said groove include a cooperating articulation for allowing relative translational movement of the first and second elements between the anterior and posterior ends and for allowing relative lateral movement of the first and second elements.

21. The prosthesis of claim 20, wherein the difference in size between the terminal end of the tongue and the opening of the groove limits the amount of said translational and lateral movement, wherein said movement is restricted when the tongue terminal end contacts the opening of the groove.

22. The prosthesis of claim 21, wherein the base of said groove is wider than the terminal end of the tongue for allowing relative axial rotation between the first and second elements.

23. The prosthesis of claim 22, wherein the difference in size between the base of said groove and the terminal end of the tongue limits the amount of said rotational movement, wherein said movement is restricted when the tongue terminal end contacts the wall forming the base of the groove.

24. The prosthesis of claim 18, wherein said recess is larger than the peg.

25. The prosthesis of claim 18, wherein the peg is provided on the second element and the recess is provided on the first element.

* * * * *